(12) United States Patent
Guy

(10) Patent No.: US 7,405,284 B2
(45) Date of Patent: Jul. 29, 2008

(54) REDUCING CELLULAR DYSFUNCTION CAUSED BY MITOCHONDRIAL GENE MUTATIONS

(75) Inventor: John Guy, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 606 days.

(21) Appl. No.: 10/687,677

(22) Filed: Oct. 17, 2003

(65) Prior Publication Data

US 2004/0142419 A1 Jul. 22, 2004

Related U.S. Application Data

(60) Provisional application No. 60/419,435, filed on Oct. 18, 2002.

(51) Int. Cl.
| | |
|---|---|
| C07H 21/02 | (2006.01) |
| C07H 21/04 | (2006.01) |
| C12N 5/00 | (2006.01) |
| C12N 5/02 | (2006.01) |
| C12N 5/08 | (2006.01) |

(52) U.S. Cl. ............... 536/23.1; 435/325; 435/366; 435/368

(58) Field of Classification Search ............... 536/23.1; 435/325, 366, 368
See application file for complete search history.

(56) References Cited

U.S. PATENT DOCUMENTS

2004/0072774 A1* 4/2004 Manfredi et al. ............ 514/44

OTHER PUBLICATIONS

Guy J., Gene therapy for nuclear complementation of the G11778A LHON mitochondrial DNA mutation, Neurology, (Apr. 24, 2001) vol. 56, No. 8 Supplement 3, pp. A14. print. Meeting Info.: 53rd Annual Meeting of the American Academy of Neurology. Philadelphia, PA, USA. May 5-11, 2001. American Academy of Neurology. (one page abstract).*
Guy et al., Rescue of a mitochondrial deficiency causing Leber Hereditary Optic Neuropathy. Ann Neurol. 52(5): 534-42, 2002, published online Oct. 11, 2002 (a cover page included).*
Guy et al., Gene therapy with the ND4 subunit gene recoded in the universal genetic code reverses a mitochondrial deficiency causing Leber Hereditary Optic Neuropathy (LHON), Neurology, (Apr. 9, 2002) vol. 58, No.7 Supplement 3, pp. A508. print. Meeting Info.: 54th Annual Meeting of the American Academy of Neurology. (one page abstract).*
Ngo, in The Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Larsson NG, Andersen O, Holme E et al. Leber's hereditary optic neuropathy and complex I deficiency in muscle. Ann Neurol. 1991; 30:701-708.

Majander A, Huoponen K, Savontaus ML et al. Electron transfer properties of NADH:ubiquinone reductase in the NDI/3460 and the ND4/11778 mutations of the Leber hereditary optic neuroretinopathy (LHON). FEBS Lett. 1991; 292:289-292.
Vergani L, Martinuzzi A, Carelli V et al. MtDNA mutations associated with Leber's hereditary optic neuropathy: studies on cytoplasmic hybrid (cybrid) cells. Biochem Biophys Res Commun. 1995; 210:880-888.
Wallace DC. Mitochondrial diseases in man and mouse. Science. 1999; 283:1482-1488.
Carelli V, Ghelli A, Bucchi L et al. Biochemical features of mtDNA 14484 (ND6/M64V) point mutation associated with Leber's hereditary optic neuropathy. Ann Neurol. 1999; 45:320-328.
Chinnery PF, Johnson MA, Wardell TM et al. The epidemiology of pathogenic mitochondrial DNA mutations. Ann Neurol. 2000; 48:188-193.
Guy J, Qi X, Hauswirth WW. Adeno-associated viral-mediated catalase expression suppresses optic neuritis in experimental allergic encephalomyelitis. Proc Natl Acad Sci U S A. 1998; 95:13847-13852.
Wallace DC, Singh G, Lott MT et al. Mitochondrial DNA mutation associated with Leber's hereditary optic neuropathy. Science. 1988; 242:1427-1430.
Hartl FU, Neupert W. Protein sorting to mitochondria: evolutionary conservations of folding and assembly. Science. 1990; 247:930-938,
Schon EA. Mitochondrial genetics and disease. Trends Biochem Sci. 2000; 25:555-560.
Guy J, Qi X, Muzyczka N et al. Reporter expression persists 1 year after adeno-associated virus- mediated gene transfer to the optic nerve. Arch Ophthalmol. 1999; 117:929-937.
Esposito LA, Melov S, Panov A et al. Mitochondrial disease in mouse results in increased oxidative stress. Proc Natl Acad Sci U S A. 1999; 96:4820-4825.
Brown MD, Trounce IA, Jun AS et al. Functional analysis of lymphoblast and cybrid mitochondria containing the 3460, 11778, or 14484 Leber's hereditary optic neuropathy mitochondrial DNA mutation. J. Biol Chem. 2000; 275:39831-39836.
Brown MD. The enigmatic relationship between mitochondrial dysfunction and Leber's hereditary optic neuropathy. J Neurol Sci. 1999; 165:1-5.
Cock HR, Cooper JM, Schapira AH. Functional consequences of the 3460-bp mitochondrial DNA mutation associated with Leber's hereditary optic neuropathy. J Neurol Sci. 1999; 165:10-17.
Sazanov, L. Resolution of the Membrane Domain of Bovine Complex I into Subcomplexes: Implications for the Structural Organization of the Enzyme. Biochemistry 2000, 39: 7229-7235.

* cited by examiner

Primary Examiner—Valarie Bertoglio
Assistant Examiner—Wu-Cheng Winston Shen
(74) Attorney, Agent, or Firm—Akerman Senterfitt; Gregory A. Nelson; Amy A. Dobbelaere

(57) ABSTRACT

A synthetic, nuclear-encoded ND4 gene was linked to a mitochondrial targeting sequence and a FLAG epitope tag. This fusion construct was inserted into a rAAV vector. The ND4 fusion protein was expressed and imported into the mitochondria of cells harboring a mitochondrial DNA mutation (G11778A), where it restored cellular respiration.

11 Claims, 3 Drawing Sheets

A

B

REDUCING CELLULAR DYSFUNCTION CAUSED BY MITOCHONDRIAL GENE MUTATIONS

CROSS-REFERENCE TO RELATED APPLICATIONS

This application claims the priority of U.S. provisional patent application No. 60/419,435, filed Oct. 18, 2002.

STATEMENT AS TO FEDERALLY SPONSORED RESEARCH

The invention was made with United States government support under grant number EY12335 awarded by the National Institutes of Health. The United States government may have certain rights in the invention.

FIELD OF THE INVENTION

The invention relates generally to the fields of cell biology, molecular genetics, and medicine. More particularly, the invention relates to compositions and methods for reducing cellular dysfunction caused by mitochondrial gene mutations.

BACKGROUND

A G to A transition at nucleotide 11778 in mitochondrial DNA (mtDNA) in the gene specifying the ND4 subunit of complex I results in an arginine to histidine substitution at amino acid 340. This mtDNA point mutation was linked to Leber Hereditary Optic Neuropathy (LHON), a maternally-inherited human disease that leads to blindness in patients during their 2nd and 3rd decades of life. Since this discovery (Wallace et al., Science 242:1427-1430, 1988), more than 30 other pathogenic point mutations in human polypeptide-coding mtDNA genes have been described. While mtDNA encodes 13 mitochondrial proteins involved in oxidative phosphorylation, the remainder of these proteins are encoded by nuclear DNA, synthesized on cytoplasmic ribosomes, and imported into the mitochondria (usually directed by an N-terminal mitochondrial targeting presequence) (Hartl et al., Science 247:930-938, 1990). Thus, mutations in either mtDNA or nuclear DNA may impair mitochondrial function and thereby result in human disease (Schon EA, Trends Biochem Sci. 25:555-560, 2000).

LHON is the most common of all mitochondrial diseases. Three mtDNA mutations (G3460A, G11778A and T14484C) account for 95% of LHON cases, with the G11778A mutation being the most common, accounting for 50% of LHON cases (Chinnery et al., Ann Neurol. 48:188-193, 2000 and Carelli et al., Ann Neurol. 45:320-328, 1999). Each of the foregoing LHON mutations affects a different subunit of the nicotinamide adenine dinucleotide::ubiquinone oxidoreductase complex (complex I) in the oxidative phosphorylation pathway, where electrons first enter the electron transport chain (Wallace DC, Science, 283:1482-1488, 1999). This large enzyme consists of 7 subunits (ND1, 2, 3, 4, 4L, 5, and 6) encoded by mtDNA, while the remaining 35 subunits are nuclear-encoded (Sazanov et al., Biochemistry 39:7229-7235, 2000). Mitochondrial oxidative phosphorylation deficiency due to mutations in complex I subunit genes is believed to play a pivotal role in development of LHON, although the precise pathophysiologic events precipitating acute visual failure and cellular injury remain incompletely understood. Each LHON mutation alters mtDNA-encoded intrinsic complex I membrane proteins, but surprisingly, results from standard spectrophotometric assays of complex I activity in LHON cells containing the G11778A mutation in the ND4 subunit gene are reduced only slightly (Vergani et al., Biochem Biophys Res Commun. 210:880-888, 1995; Majander et al., FEBS Lett. 292:289-292, 1991; and Larsson NG et al., Ann Neurol. 30:701-708, 1991). Only the G3460A mutation in the ND1 subunit gene reduces complex I activity markedly (Brown et al., J Biol. Chem., 275:39831-39836, 2000 and Cock et al., J Neurol Sci. 165:10-17, 1999). However, clear evidence of complex I deficiency with all three pathogenic mutations comes from polarographic investigations showing impairment of cellular respiration when driven by complex I linked substrates (Majander et al., FEBS Lett. 292:289-292, 1991 and Larsson N G et al., Ann Neurol. 30:701-708, 1991). How these different degrees of changes in complex I function result in the same clinical picture of almost simultaneous bilateral apoplectic visual failure during early adult life is unclear, but reductions in oxidative phosphorylation and cellular injury induced by reactive oxygen species are suspect (Esposito et al., Proc Natl Acad Sci USA 96:4820-4825, 1999 and Brown MD, J Neurol Sci. 165:1-5, 1999).

Unlike most other mitochondrial mutations that impair neurologic and myocardial function and are often fatal, patients with LHON, though blind, have a normal life expectancy. Unfortunately, there is little propensity for spontaneous visual recovery in the G11778A LHON patients, and there is no effective therapy. One of many potential avenues for treatment is to utilize gene therapy to introduce a "normal" gene encoding the defective complex I subunit into the optic nerves of LHON patients. While exogenous genes have been successfully imported into the nuclear genome to protect the optic nerve, (Guy et al., Arch Ophthalmol. 117:929-937, 1999 and Guy J, Proc Natl Acad Sci USA 95:13847-13852, 1998) these methods cannot be applied directly to similarly introduce genes into the mammalian mitochondrial genome.

SUMMARY

The invention relates to the discovery of compositions and methods for restoring normal mitochondrial function in cells having one or more mutant mtDNA genes. To restore normal mitochondrial function, the invention includes the step of introducing into the cell harboring the mutant gene a nucleic acid that complements the mutant gene. For example, the introduced nucleic acid can be one that encodes a protein that restores normal mitochondrial function to the cell harboring the mutant gene. Complementation of aberrant mitochondrial function might be overcome by introducing a complementing nucleic acid directly into cellular mitochondria.

In the invention, a nuclear-encoded version of a gene normally encoded by mtDNA is used to overcome problems associated with the differences in the genetic codes used by mtDNA and nuclear-encoded DNA. To address the other differences between mitochondrial and non-mitochondrial gene expression, the complementing nucleic acid can also include appropriate promoter, enhancer, and polyadenylation signal sequences. To target the product of the complementing nucleic acid to the mitochondria, nucleotide sequences encoding a mitochondrial targeting peptide are also included.

Accordingly, the invention features a non-naturally occurring nucleic acid that includes a nucleotide sequence which (a) encodes a functional ND4 mitochondrial protein and (b) differs from a naturally occurring nucleic acid that encodes a ND4 mitochondrial protein by at least one codon substitution. The codon substitution can be a replacement of a mitochondrial codon with a nuclear codon, e.g., UGA to UGG; AGA or AGG to UAA, UAG, or UGA; and/or AUA or AUU to AUG, CUG, or GUG. In variations of the non-naturally occurring nucleic acid, all UGA codons are substituted with UGG codons; all AGA and AGG codons are substituted with UAA, UAG, or UGA codons; and all AUA and AUU codons are substituted with AUG, CUG, or GUG codons. As one example, the non-naturally occurring nucleic acid can include the nucleotide sequence of SEQ ID NO: 1.

The non-naturally occurring nucleic acid can be contained within an expression vector such as a plasmid. It can also be contained within an rAAV virion.

The non-naturally occurring nucleic acid can also include additional elements such as a mitochondrial targeting sequence, a promoter operably linked to the nucleotide sequence, an enhancer element, and/or a polyadenylation (polyA) tail.

Also within the invention is a cell into which has been introduced a non-naturally occurring nucleic acid of the invention. The cell can be a human cell such as a human nerve cell (e.g., one located in the optic nerve of a human subject).

In another aspect the invention features a method for reducing dysfunction in a cell caused by a mtDNA mutation associated with Leber Hereditary Optic Neuropathy. This method includes the steps of: (a) providing a cell having a gene containing the mtDNA mutation; and (b) introducing into the cell a sufficient amount of a non-naturally occurring nucleic acid containing (i) a nucleotide sequence that encodes a functional ND4 mitochondrial protein and that differs from a naturally occurring nucleic acid that encodes a ND4 mitochondrial protein by at least one codon substitution and (ii) a mitochondrial targeting sequence.

Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1st edition, Springer-Verlag: New York, 2002.

By the phrase "mitochondrial codon" is meant a codon translated by a mitochondrial translation system according to the mitochondrial genetic code.

By the phrase "nuclear codon" is meant a codon translated by cellular translation system according to the standard universal genetic code.

By the term "gene" is meant a nucleic acid molecule that codes for a particular protein, or in certain cases a functional or structural RNA molecule.

As used herein, a "nucleic acid" or a "nucleic acid molecule" means a chain of two or more nucleotides such as RNA (ribonucleic acid) and DNA (deoxyribonucleic acid).

As used herein, "protein" or "polypeptide" mean any peptide-linked chain of amino acids, regardless of length or post-translational modification, e.g., glycosylation or phosphorylation. By the phrase "ND4 protein" is meant an expression product of an ND4 nucleic acid from any species, such as a native human ND4 protein, or a protein that shares at least 65% (but preferably 75, 80, 85, 90, 95, 96, 97, 98, or 99%) amino acid sequence identity with one of the foregoing and displays a functional activity of a native ND4 protein. A "functional activity" of a protein is any activity associated with the physiological function of the protein. For example, functional activities of a native ND4 protein may include facilitating cellular respiration.

As used herein, the term "vector" refers to a nucleic acid molecule capable of transporting another nucleic acid to which it has been linked. Vectors capable of directing the expression of genes to which they are operatively linked are referred to herein as "expression vectors."

The phrase "expression control sequence" refers to any genetic element (e.g., polynucleotide sequence) that can exert a regulatory effect on the replication or expression (transcription or translation) of another genetic element. Common expression control sequences include promoters, polyadenylation signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

As used herein, the terms "terminal repeat", "TR", "inverted terminal repeat" or "ITR" mean a nucleic acid sequence derived from an AAV that is required in cis for replication and packaging of AAV.

As used herein, the terms "rAAV vector" and "recombinant AAV vector" refer to a recombinant nucleic acid derived from an AAV serotype, including without limitation, AAV1, AAV2, AAV3, AAV4, AAV5, AAV6, AAV7, AAV8, etc. rAAV vectors can have one or more of the AAV WT genes deleted in whole or in part, preferably the rep and/or cap genes, but retain functional flanking ITR sequences. A "recombinant AAV virion" or "rAAV virion" is defined herein as an infectious, replication-defective virus composed of an AAV protein shell encapsulating a heterologous nucleotide sequence that is flanked on both sides by AAV ITRs.

The term "infect" is used herein to signify the entry of a virion into a host cell regardless of whether or not the virion replicates in the host cell.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1:
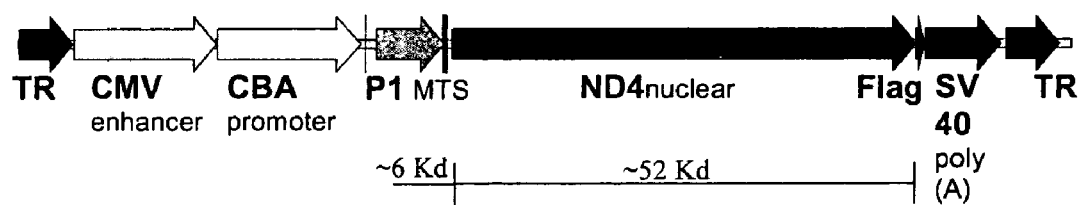
FIG. 1A is a diagram of the P1ND4FLAG construct in AAV vector UF-11.
FIG. 1B is a Western blot of ND4Flag transfected G11778A cybrids (Lanes 1-4) and untransfected controls (Lanes 5-8). P1ND4FLAG transfected cells in lanes 2-3 show a 52 Kd band that is consistent with expression of the ND4Flag fusion polypeptide, while the control cells (untransfected cells) in lanes 5-8 show no staining with the anti-FLAG antibody. The stained gel shows corresponding protein loading with successive 1 log unit dilutions. Overloading of lane 1 by cellular protein is readily apparent by the absence of any discrete pattern of protein bands in the stained gel. This is in contrast to lane 2 where discrete bands are best seen and the intensity of anti-Flag immunostaining was optimized.
Figure 1:
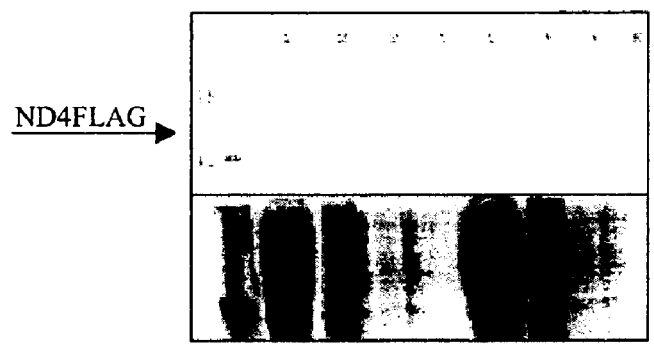

The invention encompasses compositions and methods for restoring normal mitochondrial function in cells having one or more mutant mtDNA genes, especially those associated with LHON. To restore normal mitochondrial function, a sufficient amount of a non-naturally occurring nucleic acid including a nucleotide sequence that encodes a functional mitochondrial protein that differs from a naturally occurring nucleic acid that encodes a mitochondrial protein by at least one codon substitution is introduced into a cell harboring the mtDNA mutation. The defect associated with the mutant mtDNA is thereby complemented with the non-mutant protein expressed by the non-naturally occurring nucleic acid.

Attempting this technique by using a complementing nucleic acid having the sequence of the non-mutated version of the mtDNA gene would not likely work because of the differences in the genetic codes used by mtDNA and nuclear-encoded DNA, i.e., the codons corresponding to particularly amino acids are different between mtDNA and nuclear-encoded DNA because the translation machinery for these DNAs are different. For example, simply transferring a "normal" mitochondrial ND4 gene to a cell nucleus would result in translation of a truncated protein because the UGA codon that directs insertion of a tryptophan in the mitochondria is a stop codon in the nuclear genetic code. The invention circumvents this problem by using a nuclear-encoded version of a gene normally encoded by mtDNA. To overcome the other differences between mitochondrial and non-mitochondrial gene expression, the complementing nucleic acid can also include appropriate promoter, enhancer, and polyadenylation signal sequences. To target the product of the complementing nucleic acid to the mitochondria, nucleotide sequences encoding a mitochondrial targeting peptide are also included. Utilizing these methods and compositions, diseases based on mitochondrial defects might be treated.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, $3^{rd}$ ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

ND4 Nucleic Acids

The invention provides non-naturally occurring nucleic acids that include nucleotide sequence encoding a functional ND4 mitochondrial protein. The nucleotide sequence differs from a naturally occurring nucleic acid encoding a ND4 mitochondrial protein by at least one codon substitution. A naturally occurring ND4-encoding nucleic acid is the native human nucleic acid presented herein as SEQ ID NO:2. Naturally occurring human ND4-encoding nucleic acids are also deposited with Genbank as Accession Nos. AY195778, AY195774, and AY195767. A preferred non-naturally occurring ND4-encoding nucleic acid of the invention is presented herein as SEQ ID NO: 1-an example of a nuclear-encoded version of a nucleotide sequence encoding a functional ND4 protein. This sequence contains codon substitutions that facilitate nuclear expression of a ND4 protein.

To create a nuclear-encoded version, codon substitutions are made in the mtDNA-encoding nucleic acid sequence that replace codons read by the mitochodrial genetic system with codons of the universal genetic code. Because mammalian mitochondria use a genetic code that is partially different from the universal genetic code, changes in the coding sequence of a mitochondrial gene are needed to make it compatible with the universal nuclear code. For example, the UGA codon directs insertion of a tryptophan in mitochondria but is a stop codon in the nuclear genetic code. Therefore, to create a nuclear-encoded version of a mtDNA-encoded sequence, the UGA codon of a mtDNA sequence would be substituted with UGG which codes for tryptophan in the nuclear genetic code. Codon usage in mitochondria vs. the universal genetic code is described in Lewin, Genes V, Oxford University Press: New York, 1994. Codon substitutions that might be employed include: 1) UGA to UGG, 2) AGA or AGG to UAA, UAG, or UGA, and 3) AUA or AUU to AUG.

Expression Control Sequences

In addition to the ND4-encoding nucleotide sequence, the nucleic acids of the invention can also include one or more expression control sequences operatively linked to the ND4-encoding nucleotide sequence. Numerous such sequences are known. Those to be included in the nucleic acids of the invention can be selected based on their known function in other applications. Examples of expression control sequences include promoters, insulators, silencers, IRESs, enhancers, initiation sites, termination signals, and polyA tails.

To achieve appropriate levels of ND4 proteins, any of a number of promoters suitable for use in the selected host cell may be employed. For example, constitutive promoters of different strengths can be used to express ND4 proteins.

Vectors, Viral Vectors, And Virions

The invention provides compositions and methods for introducing into cells a sufficient amount of a non-naturally occurring nucleic acid including a nucleotide sequence that encodes a functional ND4 mitochondrial protein. Thus the non-naturally occurring nucleic acid of the invention can be contained within an expression vector (e.g., plasmid) and/or encapsulated within an rAAV virion.

Expression vectors and plasmids in accordance with the present invention may include one or more constitutive promoters, such as viral promoters or promoters from mammalian genes that are generally active in promoting transcription. Examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and CMV promoters. Examples of constitutive mammalian promoters include various housekeeping gene promoters, as exemplified by the β-actin promoter. Promoters that are neither viral nor mammalian may also be used in methods of the invention. A preferred promoter for use in the invention is the constitutive chicken β-actin promoter.

For delivery to a cell, the non-naturally occurring nucleic acid of the invention might also be incorporated in a viral vector. Numerous such viral vectors are known including, for example, adenoviral vectors, lentiviral vectors, retroviral vectors, and adeno-associated virus based vectors. Based on the experiments described below, a particularly preferred vehicle for introducing a nucleic acid of the invention to a cell is an rAAV vector. An rAAV vector used in methods of the invention is a recombinant nucleic acid sequence that includes those AAV sequences required in cis for replication and packaging (e.g., functional ITRs) of the DNA into a virion. Additionally, an rAAV vector contains a non-AAV nucleic acid such as a nucleotide sequence encoding a functional ND4 protein. Useful rAAV vectors have one or more of the AAV WT genes deleted in whole or in part, but retain functional flanking ITR sequences. The AAV ITRs may be of any serotype, but in preferred methods, because they are relatively well characterized, the ITRs are derived from serotype 2. Methods for use of rAAV vectors are discussed, for example, in Tal, J., J. Biomed. Sci. 7:279-291, 2000 and Monahan and Samulski, Gene delivery 7:24-30, 2000.

An rAAV virion used in methods of the invention is an infectious virus particle containing a rAAV vector. The capsid proteins composing the exterior, non-nucleic acid portion of the virion are encoded by the AAV cap gene. The cap gene encodes three viral coat proteins, VP1, VP2 and VP3, which are required for virion assembly. The construction of rAAV virions has been described. See, e.g., U.S. Pat. Nos. 5,173, 414, 5,139,941, 5,863,541, and 5,869,305, 6,057,152, 6,376, 237; Rabinowitz et al., J. Virol. 76:791-801, 2002; and Bowles et al., J. Virol. 77:423-432, 2003.

Techniques involving AAV nucleic acids and virions of different serotypes are known in the art and are described in Halbert et al., J. Virol. 74:1524-1532, 2000; Halbert et al., J. Virol. 75:6615-6624, 2001; and Auricchio et al., Hum. Molec. Genet. 10:3075-3081, 2001. The rAAV vectors used in the invention may be derived from any of several AAV serotypes including 1, 2, 3, 4, 5, 6, 7, and 8. Preferred rAAV vectors for use in the invention are derived from serotype 2 (or mutants thereof). Particular AAV vectors and AAV proteins of different serotypes are discussed in Chao et al., Mol. Ther. 2:619-623, 2000; Davidson et al., PNAS 97:3428-3432, 2000; and Xiao et al., J. Virol. 72:2224-2232, 1998.

The rAAV vectors can further include, for example, marker or reporter genes (e.g., a nucleic acid encoding GFP) epitope tags (e.g., FLAG), MTSs (e.g., ATP1 and Aldh), and IRESs. Non-AAV nucleic acids also include, for example, therapeutic genes (e.g., a universal genetic code-compatible ND4 gene). Preferred rAAV vectors for delivering a complementary gene to a cell are constructed using plasmid pTR-UF (Klein et al., Exp. Neurol. 150:183-194, 1998; and Zolotukhin et al., J. Virol. 70:4646-4654, 1996) and contain AAV2 ITRs. For example, particularly preferred vectors of the invention include: pTR-UF11 containing the reading frame of the P1ND4Flag fusion nucleotide sequence, regulated by the 381-bp CMV immediate early gene enhancer/1352-bp chicken β-actin promoter-exon1-intron1; pTR-UF5 (Owen et al., Hum. Gene Ther. 11:2067-2078, 2000) containing an AldhND4GFP fusion nucleotide sequence; pTR-UF5 containing a COX8GFP fusion nucleotide sequence; and pTR-UF12 containing a P1ND4Flag/GFP/IRES fusion nucleotide sequence.

rAAV Mutants

Also useful in the invention are rAAV virions that have mutations within the virion capsid. For example, suitable rAAV mutants may have ligand insertion mutations for the facilitation of targeting rAAV virions to specific cell types (e.g., optic nerve cells). Pseudotyped rAAV virions that have mutations within the capsid may also be used in compositions and methods of the invention. Pseudotyped rAAV virions contain an rAAV vector derived from a particular serotype that is encapsidated within a capsid containing proteins of another serotype. Methods of making AAV capsid mutants are known, and include site-directed mutagenesis (Wu et al., J. Virol. 72:5919-5926); molecular breeding, nucleic acid, exon, and DNA family shuffling (Soong et al., Nat. Genet. 25:436-439, 2000; Coco et al., Nature Biotech. 2001; 19:354; and U.S. Pat. Nos. 5,837,458; 5,811,238; and 6,180,406; Kolkman and Stemmer, Nat. Biotech. 19:423-428, 2001; Fisch et al., Proc. Nat'l Acad. Sci. USA 93:7761-7766, 1996; Christians et al., Nat. Biotech. 17:259-264, 1999); ligand insertions (Girod et al. Nat. Med. 9:1052-1056, 1999); cassette mutagenesis (Rueda et al. Virology 263:89-99, 1999; Boyer et al., J. Virol. 66:1031-1039, 1992); and the insertion of short random oligonucleotide sequences.

Additional Vectors

In addition to AAV, Ad vectors might also be used in the invention. Methods for using recombinant Ad as gene therapy vectors are discussed, for example, in W. C. Russell, Journal of General Virology 81:2573-2604, 2000, and Bramson et al., Curr. Opin. Biotechnol. 6:590-595, 1995. Ad vectors have been shown to be capable of highly efficient gene expression in target cells and allow for a large coding capacity of heterologous DNA. An especially useful form of recombinant Ad is a "gutless", "high-capacity", or "helper-dependent" Ad vector which has all viral coding sequences deleted, and contains the viral inverted terminal repeats (ITRs), therapeutic gene (e.g., cellular respiration-enhancing gene) sequences (up to 28-32 kb) and the viral DNA packaging sequence.

Another preferred Ad vector contains a viral packaging sequence and a pair of Ad ITRs which flank a nucleotide sequence encoding a functional ND4 protein operably linked to a promoter, an enhancer, a polyA tail, and an MTS.

Herpes Simplex Virus (HSV) vectors might also be used in the invention. Methods for use of HSV vectors are discussed, for example, in Cotter and Robertson, Curr. Opin. Mol. Ther. 1:633-644, 1999. HSV vectors deleted of one or more immediate early (IE) genes are non-cytotoxic, persist in a state similar to latency in the host cell, and afford efficient host cell transduction. Recombinant HSV vectors allow for approximately 30 kb of coding capacity. A preferred HSV vector is engineered from HSV type I, is deleted of the IE genes and contains a nucleotide sequence encoding a functional ND4 protein operably linked to a promoter, an enhancer, a polyA tail, and an MTS. HSV amplicon vectors may also be used according to the invention. Typically, HSV amplicon vectors are approximately 15 kb in length, possess a viral origin of replication and packaging sequences.

The invention also provides for use of retroviral vectors, including Murine Leukemia Virus-based vectors. Methods for use of retrovirus-based vectors are discussed, for example, in Hu and Pathak, Pharmacol. Rev. 52:493-511, 2000 and Fong et al., Crit. Rev. Ther. Drug Carrier Syst. 17:1-60, 2000. Retroviral vectors according to the invention may contain up to 8 kb of heterologous (e.g., therapeutic) DNA, in place of the viral genes. Heterologous may be defined in this context as any nucleotide sequence or gene which is not native to the retrovirus. The heterologous DNA may include a tissue-specific promoter (e.g., optic nerve cell-specific) operably linked to a nucleotide sequence encoding a functional ND4 mitochondrial protein and may encode a ligand to a cell-specific receptor. The retroviral particle may be pseudotyped, and may contain a viral envelope glycoprotein from another virus, in place of the native retroviral glycoprotein. A retroviral vector useful in the invention may integrate into the genome of the host cell.

Viral vectors utilized in the present invention may also include replication-defective lentiviral vectors, including HIV. Methods for use of lentiviral vectors are discussed, for example, in Vigna and Naldini, J. Gene Med. 5:308-316, 2000 and Miyoshi et al., Journal of. Virol. 72:8150-8157, 1998. Lentiviral vectors are capable of infecting both dividing and non-dividing cells and efficient transduction of epithelial tissues of humans. HIV vectors have been shown to infect nerve cells. Lentiviral vectors according to the invention may be derived from human and non-human (including SIV) lentiviruses. A preferred lentiviral vector of the present invention may include nucleic acid sequences required for vector propagation in addition to a nucleotide sequence encoding a functional ND4 protein operably linked to a promoter, an enhancer, a polyA tail, and an MTS. These sequences may include the viral LTRs, primer binding site, polypurine tract, att sites and encapsidation site. The lentiviral vector may be packaged into any suitable lentiviral capsid. The vector capsid may contain viral envelope proteins from other viruses, including Murine Leukemia Virus (MLV) or Vesicular Stomatitis Virus (VSV). The use of the VSV G-protein yields a high vector titer and results in greater stability of the vector virus particles.

Other viral vectors that might be used in the invention are Alphaviruses, including Semliki Forest Virus (SFV) and Sindbis Virus (SIN). Methods for use of Alphaviruses are described, for example, in Lundstrom, K., Intervirology 43:247-257, 2000 and Perri et al., Journal of Virology 74:9802-9807, 2000. Alphavirus vectors typically are constructed in a format known as a replicon. Such replicons may contain Alphavirus genetic elements required for RNA replication, as well as tissue-specific (e.g., nerve cell-specific) therapeutic gene expression. The Alphavirus replicon can include a nucleotide sequence encoding a functional ND4 protein operably linked to a promoter, an enhancer, and an MTS. Recombinant, replication-defective Alphavirus vectors are capable of high-level heterologous (e.g., therapeutic) gene expression, and can infect a wide host cell range. Alphavirus replicons according to the invention may be targeted to specific cell types by displaying on their virion surface a functional heterologous ligand or binding domain that would allow selective binding to target cells expressing the cognate binding partner. Alphavirus replicons according to the invention may establish latency, and therefore long-term tissue-specific therapeutic gene expression in the host cell. The replicons may also exhibit transient tissue-specific therapeutic gene expression in the host cell. A preferred Alphavirus vector or replicon of the invention is on that is noncytopathic.

To combine advantageous properties of two viral vector systems, hybrid viral vectors may be used to deliver nucleotide sequence encoding a functional ND4 mitochondrial protein to a cell. Standard techniques for the construction of hybrid vectors are well-known to those skilled in the art. Such techniques can be found, for example, in Sambrook and Russell, supra, or any number of laboratory manuals that discuss recombinant DNA technology. Double-stranded AAV genomes in Ad capsids containing a combination of AAV and Ad ITRs may be used to transduce cells. In another variation, an AAV vector may be placed into a "gutless", "helper-dependent" or "high-capacity" Ad vector. Ad/AAV hybrid vectors are discussed in Lieber et al., J. Virol. 73:9314-9324, 1999. Retroviral/Ad hybrid vectors are discussed in Zheng et al., Nature Biotechnol. 18:176-186, 2000. Retroviral genomes contained within an Ad may integrate within the host cell genome and effect stable, tissue-specific therapeutic gene expression.

Several non-viral methods for introducing nucleic acids into host cells might also be used in the invention. For a review of non-viral methods, see Nishikawa and Huang, Human Gene Ther. 12:861-870, 2001 and M. I. Phillips, Gene Therapy Methods, Academic press, 2002. For example, various techniques employing plasmid DNA for the introduction of a nucleotide sequence encoding a functional ND4 protein operably linked to a promoter, an enhancer, a polyA tail, and an MTS into cells are provided for in the invention. Such techniques are generally known in the art and are described in references such as Ilan, Y., Curr. Opin. Mol. Ther. 1:116-120, 1999, Wolff, J. A., Neuromuscular Disord. 7:314-318, 1997 and Arztl, Z., Fortbild Qualitatssich 92:681-683, 1998.

Methods involving physical techniques for the introduction of a vector system into a host cell can be adapted for use in the present invention. The particle bombardment method of gene transfer involves an Accell device (i.e., gene gun) to accelerate DNA-coated microscopic gold particles into target tissue. Particle bombardment methods are described in Yang et al., Mol. Med. Today 2:476-481 1996 and Davidson et al., Rev. Wound Repair Regen. 6:452-459, 2000. Cell electropermeabilization (also termed cell electroporation) may be employed for delivery of a nucleotide sequence encoding a functional ND4 protein into cells of tissues. This technique is discussed in Preat, V., Ann. Pharm. Fr. 59:239-244 2001 and involves the application of pulsed electric fields to cells to enhance cell permeability, resulting in exogenous polynucleotide transit across the cytoplasmic membrane.

Synthetic gene transfer molecules according to the invention can be designed to form multimolecular aggregates with plasmid DNA (e.g., nucleotides encoding a functional ND4 protein operably linked to a promoter, enhancer, a polyA tail, and MTS) and to bind the resulting particles to the target cell surface in such a way as to trigger endocytosis and endosomal membrane disruption. Polymeric DNA-binding cations (including polylysine, protamine, and cationized albumin) can be used to trigger receptor-mediated endocytosis of nucleic acids into cells. Methods involving polymeric DNA-binding cations are reviewed in Guy et al., Mol. Biotechnol. 3:237-248, 1995 and Garnett, M. C., Crit. Rev. Ther. Drug Carrier Syst. 16:147-207, 1999. Cationic amphiphiles, including lipopolyamines and cationic lipids, may provide receptor-independent transfer of nucleic acids (e.g., a nucleotide sequence encoding a functional ND4 protein operably linked to a promoter, an enhancer, a polyA tail, and an MTS) into target cells. Preformed cationic liposomes or cationic lipids may be mixed with plasmid DNA to generate cell-transfecting complexes. Methods involving cationic lipid formulations are reviewed in Felgner et al., Ann. N.Y. Acad. Sci. 772:126-139, 1995 and Lasic and Templeton, Adv. Drug Delivery Rev. 20:221-266, 1996. Suitable methods can also include use of cationic liposomes as agents for introducing DNA or protein into cells. For therapeutic gene delivery, DNA may also be coupled to an amphipathic cationic peptide (Fominaya et al., J. Gene Med. 2:455-464, 2000).

Methods that involve both viral and non-viral based components may be used according to the invention. An Epstein Barr Virus (EBV)-based plasmid for therapeutic gene delivery is described in Cui et al., Gene Therapy 8:1508-1513, 2001. A method involving a DNA/ligand/polycationic adjunct coupled to an Ad is described in Curiel, D. T., Nat. Immun. 13:141-164, 1994.

Methods involving ultrasound contrast agent delivery vehicles may be used in the invention. Such methods are discussed in Newman et al., Echocardiography 18:339-347, 2001 and Lewin et al. Invest. Radiol. 36:9-14, 2001. Gene-bearing microbubbles, when exposed to ultrasound, cavitate and locally release a therapeutic agent. Attachment of a nerve cell-targeting moiety to the contrast agent vehicle may result in site-specific (e.g., optic nerve) therapeutic gene expression.

Reversing Cellular Dysfunction Caused by a mtDNA Mutation

The invention provides methods and compositions for reducing or reversing a cellular dysfunction caused by a mtDNA mutation. This method is illustrated by a model of the oxidative phosphorylation deficiency in LHON caused by a mutation (e.g., G11778A) in mtDNA complex I subunit genes. To reduce oxidative phosphorylation deficiency in a cell having the G1778A mutation, a non-mutated, functional copy of the corresponding gene (i.e., the ND4 gene) is introduced into the cell. Because the ND4 is a gene normally encoded by mitochondrial DNA, its genetic code differs (in part) from the universal genetic code. Thus, a preferred ND4 nucleic acid used in the invention is one that is a nuclear-encoded version of the mtDNA gene. The foregoing method can be extended to reducing dysfunction in cells caused by other mtDNA mutations.

To construct a nucleic acid that is compatible with the nuclear-encoded, universal genetic code, the approach of allotopic expression (Gray et al., Methods Enzymol. 264:369-389, 1996) can be used. This approach involves a nuclear-encoded version of a gene normally encoded by mitochondrial DNA which specifies a protein expressed in the cytoplasm that is then imported into the mitochondria. Once imported into the mitochondria, the nuclear-encoded ND4 protein can functionally replace the G1778A mutant protein in oxidative phosphorylation (e.g., to produce ATP).

Reversal or reduction of a cellular dysfunction caused by a mtDNA mutation can be assessed by known techniques. For example, to assess the reversal or reduction in the oxidative phosphorylation deficiency observed in cells having the G11778A mutation, the rate of complex I-dependent ATP synthesis (Yen et al., J Neuroophthalmol. 18:84-85, 1998; Majander et al., FEBS Lett. 412:351-354, 1997; and Lodi et al., Ann Neurol. 42:573-579, 1997) can be examined. ATP synthesis can be measured by any suitable assay, including a luciferin-luciferase assay in whole permeabilized cells using complex I substrates (e.g., malate and pyruvate) (Manfredi et al., Methods Cell Biol. 65:133-145, 2001). ATP synthesis with complex I substrates can also be measured after the addition of an ATP-ase inhibitor (e.g., 10 ng/ml oligomycin) to test for sensitivity to low doses of a specific ATPase inhibitor.

Reversing Disease Caused by a Mitochondrial Defect

Because mtDNA mutations are known to cause a variety of diseases in animal subjects, including human beings, the invention contemplates using the compositions and methods described herein for treating such diseases. As one example, a nucleic acid that complements the mutant mitochondrial gene is prepared as described above and introduced into the subject in a sufficient dose to ameliorate the symptoms of the disease. For example, to reverse the blindness in a human LHON patient, a nucleic acid that complements the specific mtDNA mutation (e.g., a nucleic acid encoding the non-mutated ND4 protein) is introduced into the optic nerve cells of the patient (e.g., by intraocular injection of rAAV vectors containing the corrective nucleic acid).

Administration of Compositions

The compositions described above may be administered to animals including human beings in any suitable formulation by any suitable method. For example, rAAV virions (i.e., particles) may be directly introduced into an animal, including by intravenous injection, intraperitoneal injection, or in situ injection into target tissue (e.g., cardiac tissue). For example, a conventional syringe and needle can be used to inject an rAAV virion suspension into an animal. Depending on the desired route of administration, injection can be in situ (i.e., to a particular tissue or location on a tissue), intramuscular, intravenous, intraperitoneal, or by another parenteral route. Parenteral administration of virions by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the rAAV virions may be in powder form (e.g., lyophilized) for constitution with a suitable vehicle, for example, sterile pyrogen-free water, before use.

To facilitate delivery of the rAAV virions to an animal, the virions of the invention can be mixed with a carrier or excipient. Carriers and excipients that might be used include saline (especially sterilized, pyrogen-free saline) saline buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly preferred for delivery of virions to human subjects. Methods for making such formulations are well known and can be found in, for example, *Remington's Pharmaceutical Sciences*.

In addition to the formulations described previously, the virions can also be formulated as a depot preparation. Such long acting formulations may be administered by implantation (for example subcutaneously or intramuscularly) or by IM injection. Thus, for example, the virions may be formulated with suitable polymeric or hydrophobic materials (for example as an emulsion in an acceptable oil) or ion exchange resins, or as sparingly soluble derivatives.

Similarly, rAAV vectors may be administered to an animal subject using a variety of methods. rAAV vectors may be directly introduced into an animal by peritoneal administration (e.g., intraperitoneal injection, oral administration), as well as parenteral administration (e.g., intravenous injection, intramuscular injection, and in situ injection into target tissue). Methods and formulations for parenteral administration described above for rAAV virions may be used to administer rAAV vectors.

Effective Doses

The compositions described above are preferably administered to a mammal in an effective amount, that is, an amount capable of producing a desirable result in a treated subject (e.g., reducing cellular dysfunction caused by mitochondrial gene mutations in the mammal). Such a therapeutically effective amount can be determined as described below.

Toxicity and therapeutic efficacy of the compositions utilized in methods of the invention can be determined by standard pharmaceutical procedures, using either cells in culture or experimental animals to determine the $LD_{50}$ (the dose lethal to 50% of the population) and the $ED_{50}$ (the dose that produces the desired effect). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of preferred compositions lies preferably within a range that includes an $ED_{50}$ with little or no toxicity. The dosage may vary within this range depending upon the dosage form employed and the route of administration utilized.

As is well known in the medical and veterinary arts, dosage for any one animal depends on many factors, including the subject's size, body surface area, age, the particular composition to be administered, time and route of administration, general health, and other drugs being administered concurrently. It is expected that an appropriate dosage for intravenous administration of the compositions would be in the range of about 5 µl/kg at $10^{13}$ particles and 50 µl/kg at $10^{12}$ particles.

EXAMPLES

The present invention is further illustrated by the following specific examples. The examples are provided for illustration only and are not to be construed as limiting the scope or content of the invention in any way.

Example 1

Materials and Methods

Construction of recoded ND4F and AAV vectors—To construct the fusion gene containing the mitochondrial targeting sequences and epitope tag, synthetic 80 mer oligonucleotide pairs were created in the nuclear genetic code and codons prevalent in highly expressed nuclear genes to conserve amino acid sequence. The synthetic oligonucleotides were overlapped by approximately 20 complementary nucleotides serving as primers for PCR with the high fidelity of pfu Turbo DNA polymerase (Stratagene, LaJolla, Calif.) until the entire 1,377 nucleotide nuclear-encoded ND4 gene was constructed. Using this technique the ND4 gene was then fused in-frame to the ATP1 or Aldh targeting sequences and FLAG or GFP 18 epitope tags. Flanking XbaI (P1 ND4Flag) or AflII and Hind III (AldhND4GFP) restriction sites were added for cloning into AAV vectors. Base deletions and substitutions in the reading frame were corrected using the QuickChange in vitro mutagenesis kit (Stratagene, LaJolla, Calif.). The entire reading frame of the P1ND4Flag fusion gene was cloned in the XbaI sites of AAV plasmid vectors pTR-UF11 (regulated by the 381-bp CMV immediate early gene enhancer/1352-bp chicken β-actin promoter-exon1-intron1). The AldhND4GFP was similarly constructed but with flanking AflII and HindIII sites for cloning into pTR-UF5.18 COX8GFP was constructed and inserted into pTR-UF5 (Owen et al., Hum Gene Ther. 11:2067-2078, 2000). To generate mitochondrially-targeted expression of P1ND4Flag and cytoplasmic-targeted expression of GFP in the same cell, the pTR-UF12 vector that had P1ND4Flag linked to GFP via a 637-bp poliovirus IRES was used. Both vectors have a splice donor/acceptor site from SV40 (16S/19S site) located just upstream of the coding sequence to aid in the nuclear expression of and transport of the message. Visualization of cytoplasmic GFP enabled the convenient identification of those cells that were also expressing P1ND4Flag, which had been inserted upstream of the IRES. The plasmids were amplified and purified by cesium chloride gradient centrifugation and then packaged into rAAV by transfection into human 293 cells using standard procedures; the rAAVs were titered by an infectious center assay (Hauswirth et al., Methods Enzymol. 316:743-761, 2000).

Cell culture and viral transfection—The study of the pathophysiology of mtDNA mutations has taken advantage of the use of transmitochondrial hybrid cell lines known as cybrids (King et al., Mitochondrial Biogenesis and Genetics, Academic Press: San Diego 264:313-334, 1996). Cybrids are created by fusion of enucleated cells from patients with mutated mtDNA, in this case the G11778A mutation, with cells that have permanently lost their mtDNA after chronic exposure to ethidium bromide. This procedure results in the production of a cell line with the mutated mtDNA of the patient and the "neutral" nuclear DNA of the host cell line. Homoplasmic osteosarcoma (143B.TK-) derived cybrids containing wild-type (11778G) or mutated (11778A) mtDNA were constructed and cultured as previously reported (Vergani et al., Biochem Biophys Res Commun. 210:880-888, 1995). For AAV infections, cybrids at approximately 80% confluency were transfected with 1 µg of DNA with TransIT Transfection Reagent (Mirus, Madison, Wis.) or $3.0 \times 10^7$ AAV or rAAV viral particles in complete high-glucose medium. Selection in galactose was performed in 10 separate wells, with the cells treated with selective medium for three days. Cells were trypsinized and counted using an automated Coulter Z-100 particle counter.

Immunological techniques—For immunohistochemistry, the transfected cybrids were trypsinized and grown on glass slides. After the cells reached confluence they were incubated for 30 min with 250 nM of the mitochondrial-specific fluorescent dye MitoTracker Red (Molecular Probes, Eugene, Oreg.). Immunostaining with mouse monoclonal anti-FLAG M2 antibodies (Sigma Immunochemicals, St. Louis, Mo.) or anti-GFP antibodies (Clontech, Carlsbad, Calif.) was performed. Secondary anti-mouse Cy5 or Cy2 and anti-rabbit Cy2 (Jackson Immunochemicals, West Grove, Pa.) were used for immunodetection. Immunofluorescence was visualized in a BioRad Confocal Microscope. The collected digital images were pseudocolored red for MitoTracker, blue or green for FLAG or green for GFP then merged in RGB format for evaluation of co-localization.

Western blots—For Western blot analysis, sonicated proteins from total cellular lysates obtained from the transfected and restrictive media selected cells were electrophoresed through a 10% polyacrylamide gel and electro-transferred to a polyvinylidene fluoride membrane (Bio-Rad, Hercules, Calif.). The membrane was immunostained with mouse monoclonal anti-FLAG M2 antibodies and then with rabbit anti-mouse IgG alkaline phosphatase-conjugated secondary antibodies. Immune complexes were detected by NBT/BCIP.

Oxidative Phosphorylation Assays—Assays of complex I activity were performed on P1ND4Flag and mock transfected cybrids in whole permeabilized cells by the reduction of cytochrome c with NADH and additionally in the presence of the inhibitor rotenone (Trounce et al., Methods Enzymol. 264:484-509, 1996). ATP synthesis was measured by a luciferin-luciferase assay in whole permeabilized cells using the complex I substrates malate and pyruvate (Manfredi et al., Methods Cell Biol. 65:133-145, 2001). ATP synthesis with malate and pyruvate was also measured after the addition of 10 ng/ml oligomycin to test for sensitivity to low doses of a specific ATPase inhibitor.

Example 2

Results

Strategy for Allotopic Expression of ND4 (FIG. 1A)—To accomplish allotopic complementation, the full-length version of nuclear-encoded ND4 was synthesized by converting the "non-standard" codons read by the mitochondrial genetic system to the universal genetic code. The nucleotide sequence of the recoded ND4 was 73% homologous to the mitochondrial version of the ND4 gene, whereas the amino acid sequences encoded by both genes were identical (FIG. 1B). Therefore, the synthetic ND4 gene encodes for a "normal" ND4 protein that is identical to the ND4 protein synthesized within mitochondria. However, the recoded ND4 protein is synthesized in the cytoplasm. To direct the import of the recoded ND4 protein into the mitochondria from the cytoplasm, an MTS specifying either the N-terminal region of 1) the P1 isoform of subunit c of human ATP synthase (ATPc) containing the entire 61-amino-acid MTS plus the first 5 amino acids of the mature P1 polypeptide 24 or 2) the aldehyde dehydrogenase (Aldh) containing the first 19 amino-acid MTS (Ni et al., J Biol. Chem. 274:12685-12691, 1999) was added. For detection of import, the short FLAG epitope tag (24 nucleotides) or to the AldhND4 gene the larger GFP tag (718 nucleotides) was added to the C-terminus of the P1ND4 gene. Although the mitochondrial import studies first began with GFP as the epitope tag, the much smaller FLAG tag was chosen for use. Even though GFP was successfully imported into mitochondria by a MTS fused to the N-terminus thus making successful transfection easily detectable in living cell culture, when GFP was fused to the C-terminus of a recoded mitochondrial gene (ATP6 or ND6) import of the fusion protein was unsuccessful (Owen et al., Hum Gene Ther. 11:2067-2078, 2000).

To achieve stable and efficient expression of the fusion gene in cells, P1ND4Flag was inserted into AAV vectors pTR-UF11 and pTR-UF12. Transgene expression in both vectors is driven by the chicken β-actin promoter and CMV enhancer. In addition, pTR-UF12 also contains an IRES linked to GFP for identification of transfected cells in living cell cultures. Thus, GFP (lacking a MTS) is expressed only in the cytoplasm, while the P1ND4Flag fusion protein is expressed in the mitochondria of the same cell. Unlike plasmid transfection that requires the addition of chemical reagents to facilitate DNA entry into cells and produces only transient and somewhat inefficient expression of the introduced gene, viral-mediated gene transfer permits efficient delivery of genes into cells for assays of transgene function (Bai et al., J Biol. Chem. 276:38808-38813, 2001). Moreover, in the case of AAV, the transferred DNA sequences may be integrated stably into the chromosomal DNA of the target cell for long-term expression of the transgene in vivo in living cells, organs, and tissues (Guy et al., Arch Ophthalmol. 117: 929-937, 1999 and Guy J, Proc Natl Acad Sci USA 95:13847-13852, 1998).

Figure 2:
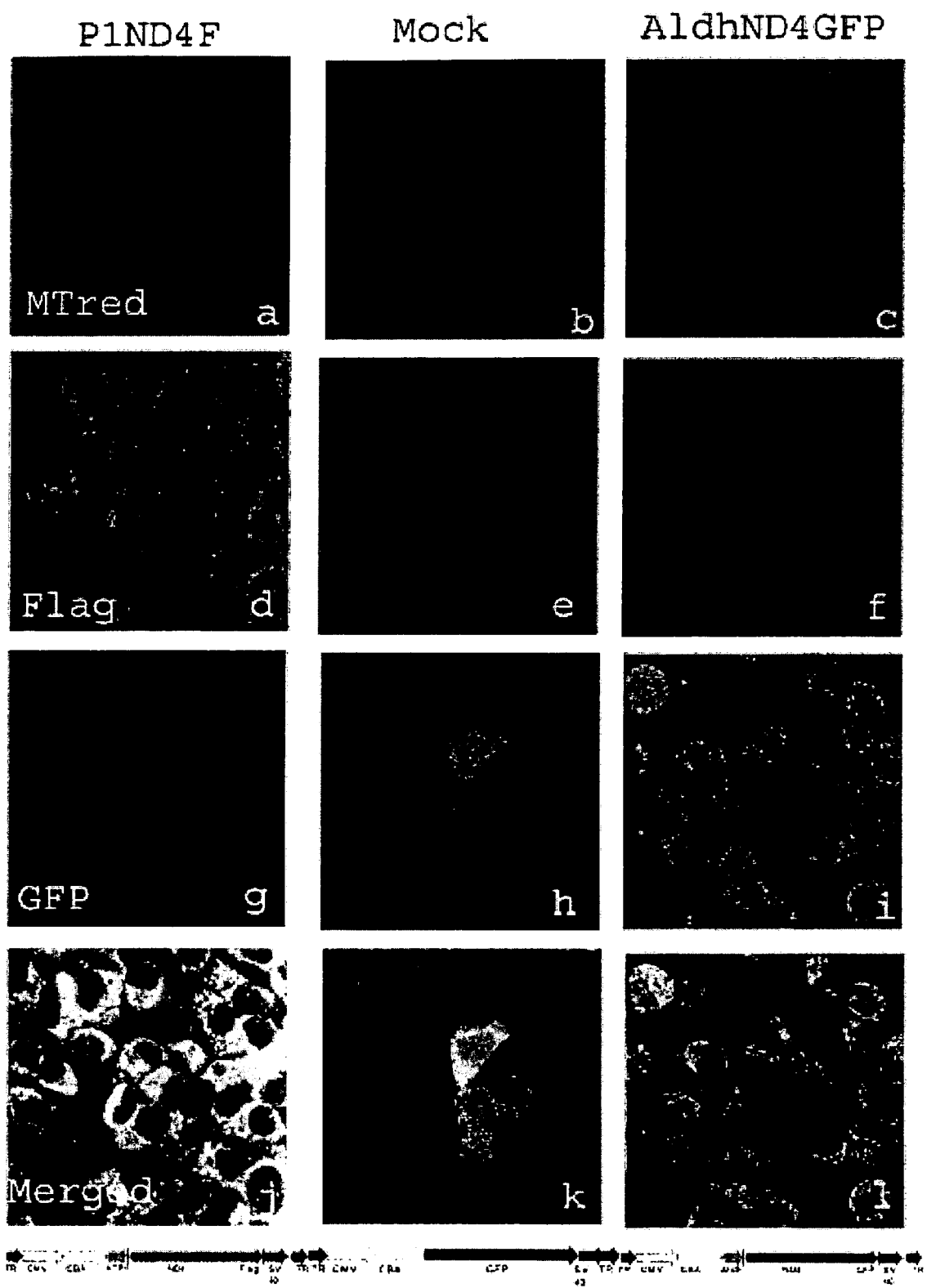
FIG. 2 is a series of microscopic images showing immunocytochemistry of G11778A LHON cybrids and maps of the constructs used in the immunocytochemical experiments. Cells were transfected with P1ND4Flag inserted into the UF-11 AAV vector (column 1), the parent UF-11 vector (with no mitochondrial targeting sequence (MTS)) (column 2), and AldhND4-Green fluorescent protein (GFP) inserted into vector UF-5 (Column 3). The cellular localization of mitochondria was visualized by MitoTracker Red (2a-c), FLAG was visualized by indirect immunofluorescence (IF) using antibodies to FLAG (2d-f), and GFP was visualized by indirect IF using antibodies to GFP (2g-i). The merged images are shown in (2j-l). Maps of the constructs used are shown below the micrographs.

Detection Of Allotopic Expression In Cells Containing Mutated mtDNA—Homoplasmic human cybrid cells containing the mitochondria of patients harboring the G11778A mutation in mtDNA transfected with rAAV containing the P1ND4Flag fusion gene expressed the fusion polypeptide (FIG. 1B). The ATPc mitochondrial targeting sequence directed the allotopically-expressed ND4F polypeptide into mitochondria. Immunocytochemistry to detect the FLAG epitope inserted at the C-terminus of the imported ND4 revealed a typical punctate mitochondrial pattern that co-localized with the mitochondrion-specific dye MitoTracker Red, thus implying the recoded ND4Flag was imported into mitochondria (FIG. 2). Cells transfected with P1ND4Flag in AAV vector UF-11 showed mitochondrially targeted FLAG (FIG. 2d) co-localized with MitoTracker Red (FIG. 2a) in the merged panel (FIG. 2j). Cells transfected with P1ND4Flag in AAV vector UF-12 that contained the IRES linked to GFP showed mitochondrially targeted FLAG and cytoplasmic GFP in the same cell. Cells mock transfected with AAV vector UF-11 driving GFP expression in the place of the P1ND4Flag gene exhibited diffuse cytoplasmic staining of GFP only (FIG. 2h). Lastly, when ND4 with the aldehyde dehydrogenase (Aldh) MTS was linked to GFP, rather than to FLAG, the ND4GFP fusion did have a punctate staining pattern import into mitochondria (FIG. 2i), but relatively poor co-localization of GFP with MitoTracker Red (FIG. 2l) suggested this fusion protein was not imported.

Figure 3:
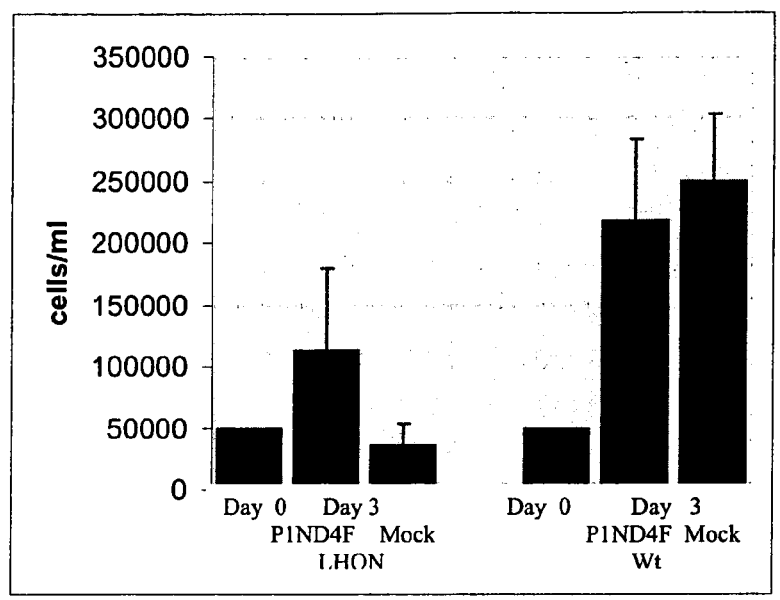
FIG. 3 is a series of bar graphs of LHON cybrid cell growth in selective media, complex I and complex V assays. A: Cell survival, after 3 days of media-selection, of G11778A cybrids and wild-type cells transfected with P1ND4Flag compared to the mock transfected cells (mean+SD, n=10). B: Bar graph showing complex I activity in whole lysed cells. Results are expressed as the total cellular complex I activity subtracted by the value obtained after the addition of the complex I inhibitor rotenone, this giving the mitochondrial component of complex I activity (Mean+SD, n=3). C: Bar graph showing the rate of ATP synthesis in permeabilized cells with pyruvate and malate serving as electron donors. Results are total ATP levels detected in a luciferin-luciferase assay and in the presence of oligomycin, an inhibitor of the mitochondrial ATP synthase (Mean+SD). (RLU=relative light units).
Figure 3:
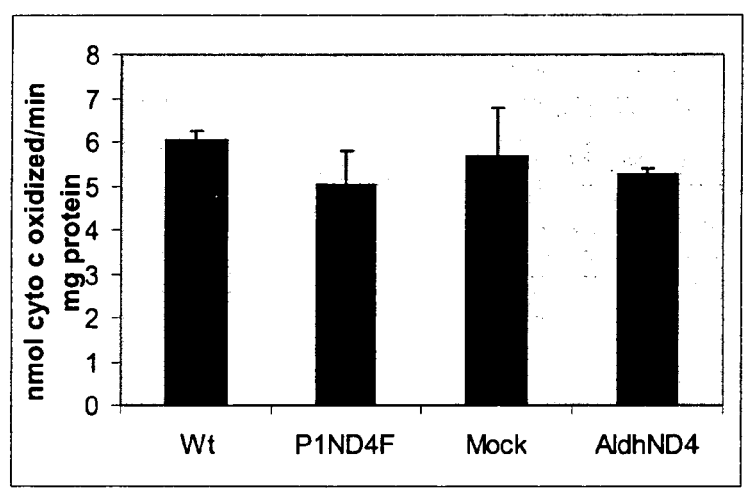
Figure 3:
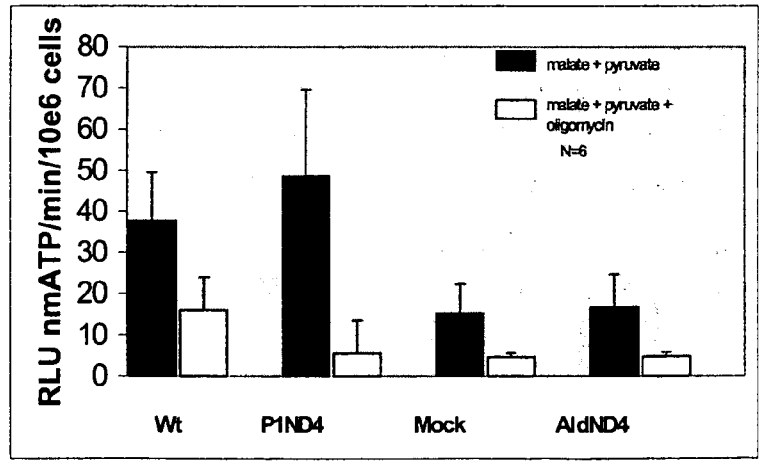

Allotopic ND4 Improves Cybrid Cell Survival—While P1ND4Flag was expressed and imported into mitochondria, the question of whether or not allotopic complementation with this protein would improve the defective oxidative phosphorylation of LHON was addressed. To answer this question, homoplasmic cybrid cells harboring mutant mtDNA (i.e. 100% G1778A derived from a patient with LHON inserted into a neutral nuclear background) were transfected with rAAV containing the P1ND4Flag or mock-transfected with the same AAV plasmid lacking the allotopic insert and expressing GFP (UF-11). Immediately following the transfection, cells were grown in glucose-rich media for 3 days, then placed in glucose-free media containing galactose as the main carbon source for glycolysis. This media forces the cells to rely predominantly on oxidative phosphorylation to produce ATP (Reitzer et al., J Biol. Chem. 254:2669-2676, 1979). Cells harboring complex I mutations have a severe growth defect compared to wild-type cells in such medium (Bai et al., J Biol. Chem. 276:38808-38813, 2001). Cybrid cell survival after 3 days in the glucose-deficient galactose media was 3-fold greater for the allotopically transfected P1ND4Flag cybrids than were the cybrids transfected with the mock AAV (p<0.001) (FIG. 3A). Apparently, in the mutated cybrids this selection enriched for cells that expressed higher levels of P1ND4Flag, suggesting these cells likely had improved oxidative phosphorylation.

Oxidative Phosphorylation Deficiency Rescued By Allotopic ND4—Consistent with the finding that spectrophotometric assays of complex I activity do not discriminate between wild-type cells and G11778A mutant cybrids, (Majander et al., FEBS Lett. 292:289-292, 1991; Brown et al., J Biol. Chem., 275:39831-39836, 2000; Andreu et al., Ann Neurol. 45:820-823, 1999; and Hofhaus et al., J Biol. Chem. 271:13155-13161, 1996) transfection with P1ND4Flag did not increase complex I activity (FIG. 3B). These results are in accord with published observations that the impact of the G1778A LHON mutation on complex I specific activity in cell lines appears to be mild (Brown et al., J Biol. Chem., 275:39831-39836, 2000 and Hofhaus et al., J Biol. Chem. 271:13155-13161, 1996). Therefore, changes in ATP synthesis using malate and pyruvate as complex I substrates for oxidative phosphorylation were focused on (FIG. 3C) (Larsson N G et al., Ann Neurol. 30:701-708, 1991). It has been shown that respiration of G11778A cell lines is reduced with complex I substrates, but may be increased with complex II substrates due perhaps to compensatory regulation of the nuclear-encoded complex II (Majander et al., FEBS Lett. 292:289-292, 1991; Larsson et al., Ann Neurol. 30:701-708, 1991; and Yen et al., Br J Ophthalmol. 80:78-81, 1996). Consistent with these observations, relative to the wild-type cell line with normal mtDNA, cybrid cells containing the LHON G11778A mutation in mitochondrial DNA showed a 60% reduction in the rate of complex I-dependent ATP synthesis (p<0.005) (Yen et al., J Neuroophthalmol. 18:84-85, 1998; Majander et al., FEBS Lett. 412:351-354, 1997; and Lodi et al., Ann Neurol. 42:573-579, 1997). Moreover, using the complex II substrate succinate which bypasses the mutated complex I, ATP synthesis in G1778A cybrids increased 5-fold (82 Relative Light Units/nmATP/min/$10^6$ cells with succinate vs 31 RLU nmATP/min/$10^6$ cells with malate and pyruvate, p<0.02). However, in the wild-type cell line containing normal mtDNA, the rates of ATP synthesis obtained with either complex I or complex II substrates were virtually identical (30.8 RLU/nmATP/min/$10^6$ cells with succinate vs 31.4 RLU nmATP/min/$10^6$ cells with malate and pyruvate).

Although complex II-dependent ATP synthesis was actually increased more than 2-fold (p<0.05) in the LHON cybrids relative to the wild-type cell line, this finding was likely compensatory as previously demonstrated (Majander et al., FEBS Lett. 292:289-292, 1991; Larsson et al., Ann Neurol. 30:701-708, 1991; and Yen et al., Br J Ophthalmol. 80:78-81, 1996). Attention was therefore focused on the main problem, the deficiency in complex I-dependent ATP synthesis induced by the G11778A mutation in the mitochondrial gene for complex I. Such substantial reductions in ATP synthesis likely contribute to the development of optic neuropathy in LHON patients with the G11778A mutation, but whether or not allotopic expression of a normal ND4 gene would rescue the substantial deficiency in complex I-dependent ATP synthesis of LHON cybrids needed to be investigated. Indeed, relative to G1778A cybrids transfected with a mock AAV vector lacking the P1ND4Flag gene, P1ND4Flag complemented G11778A cybrids showed a 3-fold increase in the rate of ATP synthesis. This degree of recovery led to levels of ATP synthesis that were virtually indistinguishable from the corresponding wild-type cell line containing normal mtDNA. While the level of transfection by AAV containing P1ND4flag is somewhat variable, as shown by higher standard deviations obtained with this construct, the differences between P1ND4flag and mock-transfected cybrids were statistically significant (p<0.02), thus P1ND4flag has a major impact on ATP synthesis. In contrast, when the AldhND4GFP construct was tested, cytoplasmic expression of ND4 had no impact on ATP levels, as predicted by the lack of mitochondrial import (FIG. 21).

Other Embodiments

It is to be understood that while the invention has been described in conjunction with the detailed description thereof, the foregoing description is intended to illustrate and not limit the scope of the invention, which is defined by the scope of the appended claims. Others aspects, advantages, and modifications are within the scope of the following claims.

What is claimed is:

1. An isolated nucleic acid comprising a nucleotide sequence encoding a functional ND4 mitochondrial protein, wherein the nucleotide sequence comprises the sequence of SEQ ID NO:1.

2. The isolated nucleic acid of claim 1, wherein the nucleic acid is comprised within an expression vector.

3. The isolated nucleic acid of claim 2, wherein the expression vector is a plasmid.

4. The isolated nucleic acid of claim 1, wherein the nucleic acid is comprised within an rAAV virion.

5. The isolated nucleic acid of claim 1, wherein the nucleic acid further comprises a nucleotide sequence encoding a mitochondrial targeting sequence.

6. The isolated nucleic acid of claim 1, wherein the nucleic acid further comprises a promoter operably linked to the nucleotide sequence.

7. The isolated nucleic acid of claim 1, wherein the nucleic acid further comprises an enhancer element.

8. The isolated nucleic acid of claim 1, wherein the nucleic acid further comprises a polyA tail.

9. An isolated cell into which has been introduced a nucleic acid comprising a nucleotide sequence encoding a functional ND4 mitochondrial protein wherein the nucleotide sequence comprises the sequence of SEQ ID NO: 1.

10. The cell of claim 9, wherein the cell is a human cell.

11. The cell of claim 10, wherein the cell is a human nerve cell.

* * * * *

UNITED STATES PATENT AND TRADEMARK OFFICE
CERTIFICATE OF CORRECTION

PATENT NO.        : 7,405,284 B2                              Page 1 of 1
APPLICATION NO.   : 10/687677
DATED             : July 29, 2008
INVENTOR(S)       : John Guy It is certified that error appears in the above-identified patent and that said Letters Patent is hereby corrected as shown below:

Col. 1, Line 14-17
In the section, STATEMENT AS TO FEDERALLY SPONSORED RESEARCH, replace "The invention was made with United States government support under grant number EY12335 awarded by the National Institutes of Health. The United States government may have certain rights in the invention." with -- The invention was made with United States government support under grant number EY12335 awarded by the National Institutes of Health. The United States government has certain rights in the invention. --

Signed and Sealed this

Seventh Day of October, 2008

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 1377
<212> TYPE: DNA
<213> ORGANISM: Homo sapiens

<400> SEQUENCE: 1
atgctgaagc tgatcgtgcc cacaatcatg ctgctgcccc tgacatggct gagcaagaag      60
cacatgatct ggatcaacac aacaacacac agcctgatca tcagcatcat ccccctgctg     120
ttcttcaacc agatcaacaa caacctgttc agctgcagcc ccacattcag cagcgacccc    180
ctgacaacac ccctgctgat gctgacaaca tggctgctgc ccctgacaat catggctagc    240
```

| | |
|---|---|
| cagaggcacc tgagcagcga gccccctgagc aggaagaagc tgtacctgag catgctgatc | 300 |
| agcctgcaga tcagcctgat catgacattc acagctacag agctgatcat gttctacatc | 360 |
| ttcttcgaga caacactgat ccccacactg gctatcatca aaggtgggg caaccagccc | 420 |
| gagaggctga acgctggcac atacttcctg ttctacacac tggtgggcag cctgcccctg | 480 |
| ctgatcgctc tgatctacac acacaacaca ctgggcagcc tgaacatcct gctgctgaca | 540 |
| ctgacagctc aggagctgag caacagctgg gctaacaacc tgatgtggct ggcttacaca | 600 |
| atggctttca tggtgaagat gcccctgtac ggcctgcacc tgtggctgcc caaggctcac | 660 |
| gtggaggctc ccatcgctgg cagcatggtg ctggctgctg tgctgctgaa gctgggcggc | 720 |
| tacggcatga tgaggctgac actgatcctg aacccctga caaagcacat ggcttacccc | 780 |
| ttcctggtgc tgagcctgtg gggcatgatc atgacaagca gcatctgcct gaggcagaca | 840 |
| gacctgaaga gcctgatcgc ttacagcagc atcagccaca tggctctggt ggtgacagct | 900 |
| atcctgatcc agacaccctg gagcttcaca ggcgctgtga tcctgatgat cgctcacggc | 960 |
| ctgacaagca gcctgctgtt ctgcctggct aacagcaact acgagaggac acacagcagg | 1020 |
| atcatgatct tgagccaggg cctgcagaca ctgctgcccc tgatggcttt ctggtggctg | 1080 |
| ctggctagcc tggctaacct ggctctgccc cccacaatca acctgctggg cgagctgagc | 1140 |
| gtgctggtga caacattcag ctggagcaac atcacactgc tgctgacagg cctgaacatg | 1200 |
| ctggtgacag ctctgtacag cctgtacatg ttcacaacaa cacagtgggg cagcctgaca | 1260 |
| caccacatca caacatgaa gcccagcttc acaagggaga acacactgat gttcatgcac | 1320 |
| ctgagcccca tcctgctgct gagcctgaac cccgacatca tcacaggctt cagcagc | 1377 |

<210> SEQ ID NO 2
<211> LENGTH: 1378
<212> TYPE: DNA
<213> ORGANISM: Homo sapiens

<400> SEQUENCE: 2

| | |
|---|---|
| atgctaaaac taatcgtccc aacaattata ttactaccac tgacatgact ttccaaaaaa | 60 |
| cacataattt gaatcaacac aaccacccac agcctaatta ttagcatcat ccctctacta | 120 |
| ttttttaacc aaatcaacaa caacctattt agctgttccc caaccttttc ctccgacccc | 180 |
| ctaacaaccc ccctcctaat actaactacc tgactcctac ccctcacaat catggcaagc | 240 |
| caacgccact tatccagtga accactatca cgaaaaaaac tctacctctc tatactaatc | 300 |
| tccctacaaa tctccttaat tataacattc acagccacag aactaatcat attttatatc | 360 |
| ttcttcgaaa ccacacttat ccccaccttg gctatcatca cccgatgagg caaccagcca | 420 |
| gaacgcctga acgcaggcac atacttccta ttctacaccc tagtaggctc ccttcccta | 480 |
| ctcatcgcac taatttacac tcacaacacc ctaggctcac taaacattct actactcact | 540 |
| ctcactgccc aagaactatc aaactcctga gccataact taatatgact agcttacaca | 600 |
| atagcttta tagtaaagat acctctttac ggactccact tatgactccc taaagcccat | 660 |
| gtcgaagccc ccatcgctgg gtcaatagta cttgccgcag tactcttaaa actaggcggc | 720 |
| tatggtataa tacgcctcac actcattctc aaccccctga caaaacacat agcctacccc | 780 |
| ttccttgtac tatccctatg aggcataatt ataacaagct ccatctgcct acgacaaaca | 840 |
| gacctaaaat cgctcattgc atactcttca atcagccaca tagccctcgt agtaacagcc | 900 |
| attctcatcc aaacccctg aagcttcacc ggcgcagtca ttctcataat cgcccacggg | 960 |
| cttacatcct cattactatt ctgcctagca aactcaaact acgaacgcac tcacagtcgc | 1020 |

-continued

```
atcataatcc tctctcaagg acttcaaact ctactcccac taatagcttt ttgatgactt   1080
ctagcaagcc tcgctaacct cgccttaccc cccactatta acctactggg agaactctct   1140
gtgctagtaa ccacgttctc ctgatcaaat atcactctcc tacttacagg actcaacata   1200
ctagtcacag ccctatactc cctctacata tttaccacaa cacaatgggg ctcactcacc   1260
caccacatta acaacataaa accctcattc acacgagaaa acaccctcat gttcatacac   1320
ctatccccca ttctcctcct atccctcaac cccgacatca ttaccgggtt ttcctctt    1378
```